United States Patent
Kupryushkin et al.

(10) Patent No.: US 11,643,433 B2
(45) Date of Patent: May 9, 2023

(54) METHOD FOR TEMPLATE-BASED ENZYMATIC DNA SYNTHESIS USING PHOSPHORYL GUANIDINE OLIGONUCLEOTIDES AND REACTION MIXTURES FOR CARRYING OUT THE METHOD

(71) Applicants: "BIOLABMIX" LLC, Novosibirsk (RU); "NOOGEN" LLC, Novosibirsk (RU)

(72) Inventors: Maxim Sergeevich Kupryushkin, Novosibirsk (RU); Inna Alekseevna Pyshnaya, Novosibirsk (RU); Elena Vladimirovna Dmitrienko, Novosibirsk (RU); Dmitry Aleksandrovich Stetsenko, Novosibirsk (RU); Maksim Leonidovich Filipenko, Novosibirsk (RU); Igor Petrovich Oscorbin, Novosibirsk (RU); Grigory Aleksandrovich Stepanov, Berdsk (RU); Vladimir Aleksandrovich Richter, Novosibirsk (RU); Mikhail Konstantinovich Ivanov, Koltsovo (RU); Dmitrii Vladimirovich Pyshnyi, Novosibirsk (RU)

(73) Assignees: "BIOLABMIX" LLC, Novosibirsk (RU); "NOOGEN" LLC, Novosibirsk (RU)

(*) Notice: Subject to any disclaimer, the term of this patent is extended or adjusted under 35 U.S.C. 154(b) by 215 days.

(21) Appl. No.: 16/769,680

(22) PCT Filed: Sep. 17, 2018

(86) PCT No.: PCT/RU2018/050115
§ 371 (c)(1),
(2) Date: Jun. 4, 2020

(87) PCT Pub. No.: WO2019/112485
PCT Pub. Date: Jun. 13, 2019

(65) Prior Publication Data
US 2020/0369709 A1    Nov. 26, 2020

(30) Foreign Application Priority Data

Apr. 12, 2017 (RU) .................. 2017140645

(51) Int. Cl.
*C07H 21/00* (2006.01)
*C12P 19/34* (2006.01)

(52) U.S. Cl.
CPC .............. *C07H 21/00* (2013.01); *C12P 19/34* (2013.01)

(58) Field of Classification Search
CPC ........ C07H 21/00; C12P 19/34; C12Q 1/6869
See application file for complete search history.

(56) References Cited

U.S. PATENT DOCUMENTS 8,334,099 B2    12/2012    Bi
2017/0015699 A1    1/2017    Chan et al.

FOREIGN PATENT DOCUMENTS

WO    WO-2013/091835 A1    6/2013
WO    WO-2013/140107 A1    9/2013
WO    WO-2016/028187 A1    2/2016

OTHER PUBLICATIONS

Saiki R.K., Scharf S., Faloona F., Mullis K.B., Hom G.T., Erlich H.A., Arnheim N. Enzymatic amplification of beta-globin genomic sequences and restriction site analysis for diagnosis of sickle cell anemia // Science.—1985.—V. 230.—p. 1350-1354.
Mullis K.B., Faloona F.A. Specific synthesis of DNA in vitro via a polymerase-catalyzed chain reaction // Methods Enzymol.—1987.—V. 155.—p. 335-350.
Ballantyne K.N., van Oorschot R.A., Mitchell R.J. Locked nucleic acids in PCR primers increase sensitivity and performance // Genomics.—2008.—V. 91.—p. 301-305.
Brent C. Satterfield cooperative primers : 2.5 million-fold improvement in the reduction of non-specific amplification//J. Mol. Diagn.—2014.—V. 16.—p. 163-173.
Schneider U.V., Mikkelsen N.D., Lindqvist A., Okkels L.M., Jøhnk N., Lisby G. Improved efficiency and robustness in qPCR and multiplex end-point PCR by twisted intercalating nucleic acid modified primers // PLoS One.—2012.—V. 7.—e38451.
Lebedev A.V., Paul N., Yee J., Timoshchuk V.A., Shum J., Miyagi K., Kellum J., Hogrefe R.I., Zon G. Hot start PCR with heat-activatable primers: a novel approach for improved PCR performance // Nucleic Acids Res.—2008.—V. 36.—e131.
Summerton J., Stein D., Huang S.B., Matthews P., Weller D., Partridge M. Morpholino and phosphorothioate antisense oligomers compared in cell-free and in-cell systems // Antisense Nucleic Acid Drug Dev.—1997.—V. 7.—p. 63-70.
Kupryushkin MS, Pyshnyi DV, Stetsenko D.A. Phosphoryl guanidines. A new class of nucleic acid analogues // Acta Naturae.—2014.—V. 6.—No. 4.—p. 116-118.

(Continued)

*Primary Examiner* — Jezia Riley
(74) *Attorney, Agent, or Firm* — Muncy, Geissler, Olds & Lowe, P.C.

(57) ABSTRACT

The invention relates to the development and optimization of PCR and RT-PCR systems used to detect nucleic acids, including the diagnosis of genetic, viral, and other diseases. The essence of the proposed method is that neutral derivatives of oligonucleotides, namely phosphoryl guanidines containing one or more phosphate groups in which guanidine or substituted guanidine residue is introduced on the phosphorus atom, are used as primers for the template-based amplification, including polymerase chain reaction (PCR) and PCR combined with reverse transcription (RT-PCR). The invention allows to obtain more reliable, specific and selective results in the process of PCR, in particular, to increase the sensitivity of PCR by reducing the yield of by-products of DNA amplification and/or to control the yield of the PCR product, including intentionally suppressing, by using different combinations of the location and number of modified phosphate groups in the oligonucleotide primers.

9 Claims, 13 Drawing Sheets

(56) References Cited

OTHER PUBLICATIONS

Kuznetsov N.A., Kupryushkin M.S., Abramova T.V., Kuznetsova A.A., Miroshnikova A.D., Stetsenko D.A., Pyshnyi D.V, Fedorova O.S.
New Oligonucleotide Derivatives as Unreactive Substrate Analogues and Potential Inhibitors of Human Apurinic/Apyrimidinic Endonuclease APE1, Kuznetsova A.A. Molecular BioSystems.—2016.—V. 12.—N 1.—p. 67-75.

A
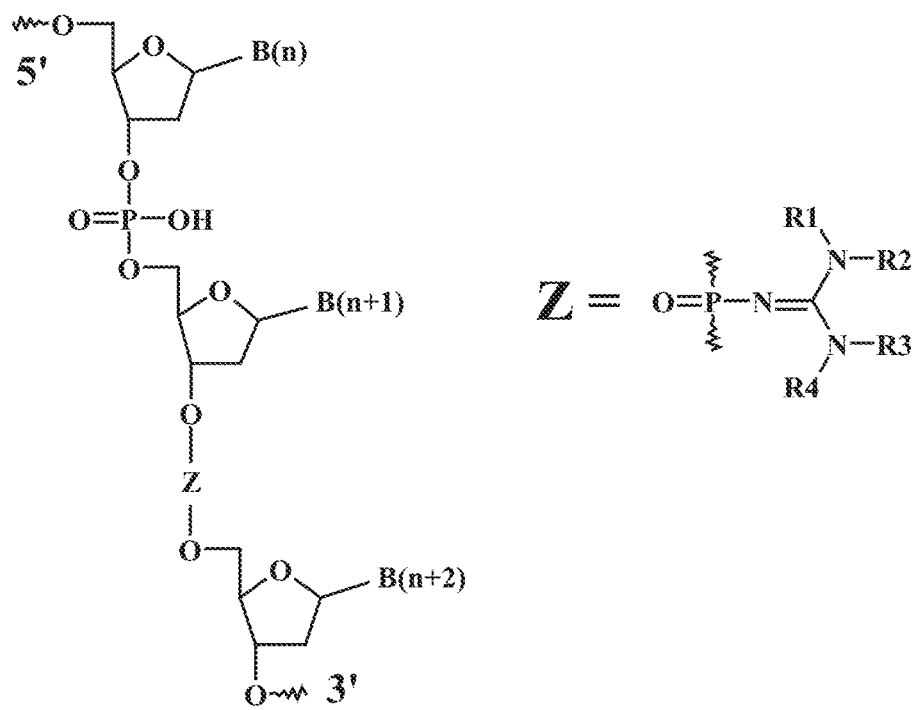
B
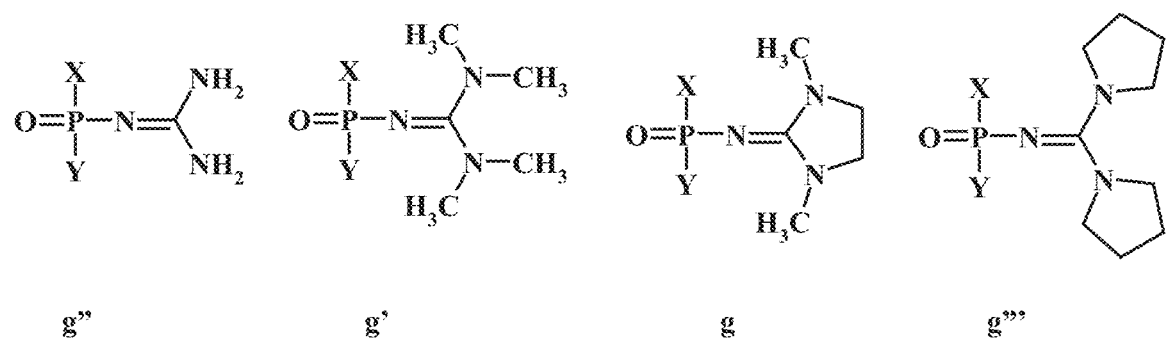
FIG. 1

|  | Designation | Sequence in the direction 5'→3' |
|---|---|---|
| Native oligonucleotides | Z0 | GpGpTpGpCpGpCpTpCpCpTpGpGpApCpGpTpApGpC |
|  | Q0 | *GpTpApApApCpGpGpCpCpApCpApApGpTpTpCpApG |
|  | P0 | pCpApCpTpCpGpCpApApGpCpApCpCpTpApTpCpApG |
|  | M30 | CpTpGpTpTpGpTpTpTpApGpCpTpApCpGpTpCpCpApGpGpApGpCpGpCpApCpC |
|  | M40 | GpTpTpGpCpGpApApApGpTpTpGpCpGpApApApCpApApApApApApApApApApApApApApApApApApC |
|  | N8 | FAMpGpCpTpApCpGpTpC |
|  | T0 | [32P]TpTpTpTpTpTpTpTpTpTpTpTpTpTpTpTpTpTpTp |
|  | U0 | GpCpCpTpTpApApApCpTpTpApTpGpApGpTpApApGpG |
|  | V0 | CpGpGppGpCpApGpApTpCpGpCpApC |
|  | D0 | GpTpApApApApCpGpApCpGpGpCpCpApGpT |
|  | S | CpApTpApTpTpCpGpTpCpCpApCpApApApApApTpGpApTpTpCpTpG |
|  | S0 | GpTpGpGpTpApGpTpTpGpGpApGpCpTpGpGpApGpA |
| PG-oligonucleotides | T1 | [32P]TpTpTpTpTpTpTpTpTpTpTpTpTpTpTpTpTpTpTgTp |
|  | T2 | [32P]TpTpTpTpTpTpTpTpTpTgTpTpTpTpTpTpTpTpTp |
|  | T3 | [32P]TpTpTpTpTpTpTpTpTpTgTpTpTpTpTpTpTpTpTp |
|  | Z1 | GpGpTpGpCpGpCpTpCpCpTpGpGpApCpGpTpApGgC |
|  | Z2 | GpGpTpGpCpGpCpTpCpCpTpGpGpApCpGpTpAgGpC |
|  | Z3 | GpGpTpGpCpGpCpTpCpCpTpGpGpApCpGpTgApGpC |
|  | Z4 | GpGpTpGpCpGpCpTpCpCpTpGpGpApCpGgTpApGpC |
|  | Z5 | GpGpTpGpCpGpCpTpCpCpTpGpGpApCgGpTpApGpC |
|  | Z6 | GpGpTpGpCpGpCpTpCpCpTpGpGpApGCpGpTpApGpC |
|  | Z7 | GpGpTpGpCpGpCpTpCpCpTpGpGpGgApCpGpTpApGpC |
|  | Z8 | GpGpTpGpCpGpCpTpCpCpTpGgGpApCpGpTpApGpC |
|  | Z9 | GpGpTpGpCpGpCpTpCpCpTgGpGpApCpGpTpApGpC |
|  | Z8,9 | GpGpTpGpCpGpCpTpCpCpTgGgGpApCpGpTpApGpC |
|  | Z1,2 | GpGpTpGpCpGpCpTpCpCpTpGpGpApCpGpTpAgGgC |
|  | Z1,3 | GpGpTpGpCpGpCpTpCpCpTpGpGpApCpGpTgApGgC |
|  | ZH1 | GgGgTgGgCgGgCgTgCgCgTgGpGpApCpGpTpApGpC |
|  | ZH2 | GgGpTgGpCgGpCgTpCgCpTgGpGpApCpGpTpApGpC |
|  | ZF | GgGpTgGpCgGpCgTpCgCpTgGpGgApCgGpTgApGgC |
|  | QH2 | GgTpAgApAgCpGgGpCgCpAgCpApApGpTpTpCpApG |
|  | UH1 | GgCpCgTpTgApAgApCgTpTgApTpGpApGpTpApApGpG |
|  | VH1 | CgGpGgGpCgApGgApTpCpGpCpApApC |
|  | WH1 | AgGpAgTpCgGpCgApAgCpTgCpCpCpApGpGpCpApTpC |
|  | P7 | *CgAgCgTgCgGgCpApApGpCpApCpCpTpApTpCpApG |
|  | P9 | *CgAgCgTgCgGgCgAgApGpCpApCpCpTpApTpCpApG |
|  | P11 | *CgAgCgTgCgGgCgAgAgGgCpCpCpTpApTpCpApG |
|  | P13 | *CgAgCgTgCgGgCgAgAgGgCgAgCpCpTpApTpCpApG |
|  | P15 | *CgAgCgTgCgGgCgAgAgGgCgAgCgCgTpApTpCpApG |
|  | P17 | *CgAgCgTgCgGgCgAgAgGgCgAgCgCgTgApTpCpApG |
|  | P2 | *CgAgCgTgCgGgCgAgAgGgCgAgCgCgTgAgTpCpApG |
|  | P22 | *CgAgCgTgCgGgCgAgAgGgCgAgCgCgTgAgTgCpApG |
|  | P23 | *CgAgCgTgCgGgCgAgAgGgCgAgCgCgTgAgTgCgApG |
|  | P24 | *CgAgCgTgCgGgCgAgAgGgCgAgCgCgTgAgTgCgAgG |
|  | D2 | GpTpApApApApCpGpApCpGpGpCpCpAgGgT |
|  | D3 | GpTpApApApApCpGpApCpGpGpCpCpCgAgGgT |
|  | S1 | GpTpGpGpTpApGpTpTpGpGpApGpCpTpGpGpTgGpA |
|  | S0 | GpApCpTpGpApApTpApTpApApApCpTpTpGpGpGpTpApGpTpTG |
|  | S | CpApTpApTpTpCpGpTpCpCpApCpApApApApApTpGpApTpTpCpTpG |

FIG. 2

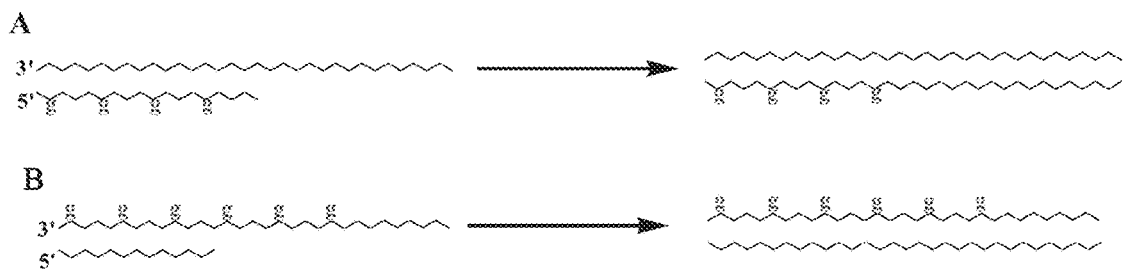
FIG. 3
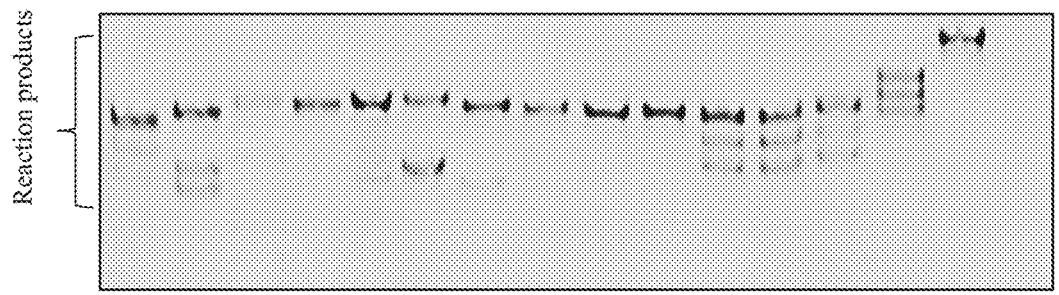
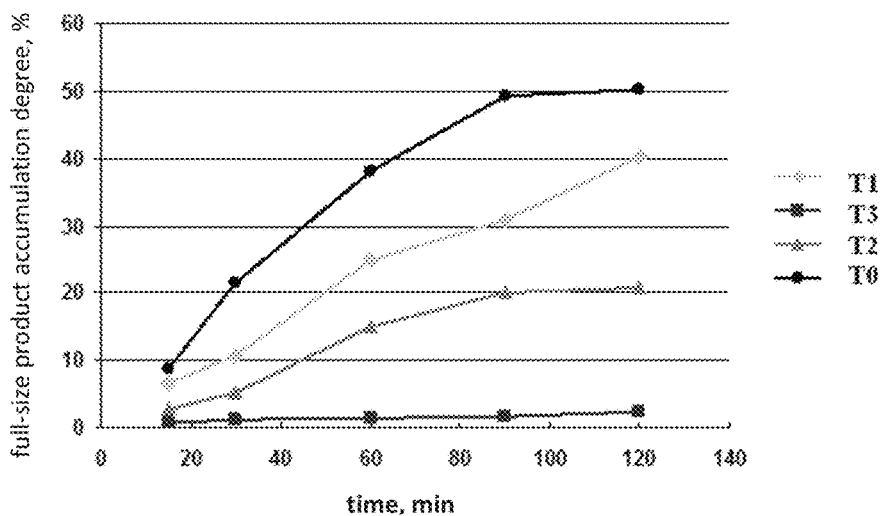
FIG. 4.

| Forward primer | Reverse primer | $k_{eff}$ | SD |
|---|---|---|---|
| Q0 | Z0 | 1.94 | 0.061 |
| | Z1 | 1.82 | 0.006 |
| | Z2 | 1.80 | 0.035 |
| | Z3 | 1.88 | 0.023 |
| | Z4 | 1.73 | 0.026 |
| | Z5 | 1.76 | 0.045 |
| | Z6 | 1.86 | 0.025 |
| | Z7 | 1.87 | 0.025 |
| | Z8 | 1.87 | 0.012 |
| | Z9 | 1.88 | 0.006 |
| | ZH1 | 1.40 | 0.046 |
| | ZH2 | 1.84 | 0.024 |
| | Z1,2 | N/A | N/A |
| | Z1,3 | 1.63 | 0.023 |
| | Z8,9 | 1.86 | <0.006 |
| | ZF | N/A | N/A |
| QH2 | Z0 | 1.86 | <0.006 |

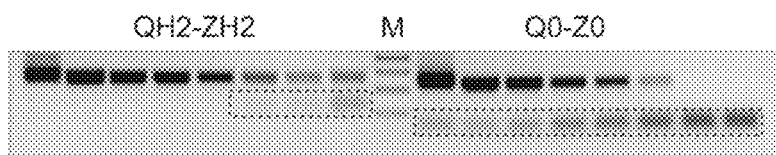
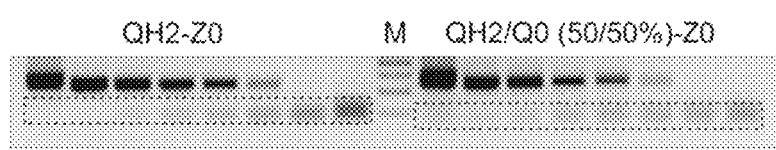
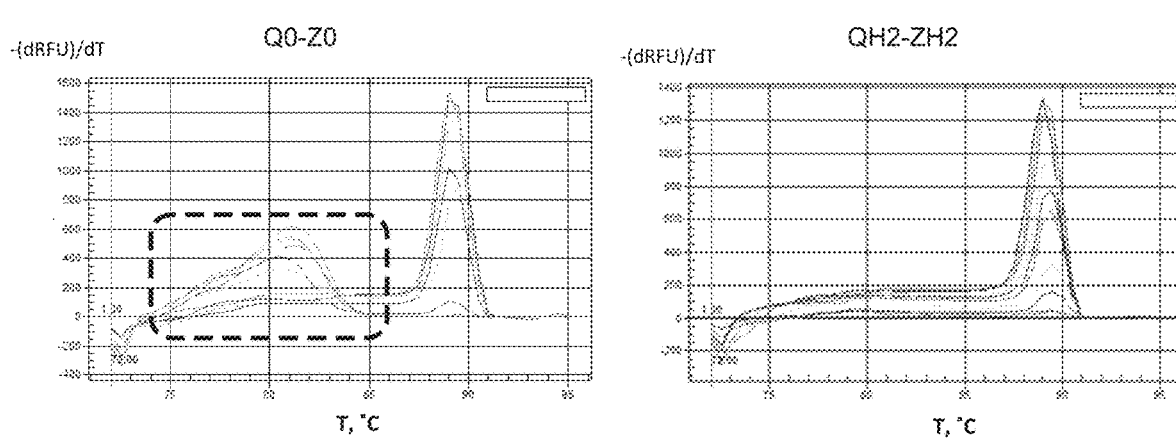
FIG. 10.

A
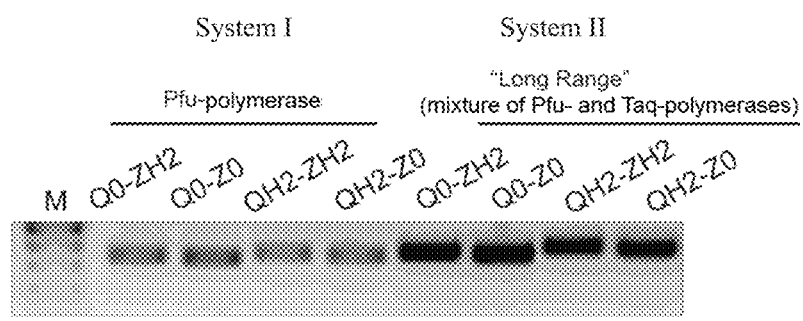
B
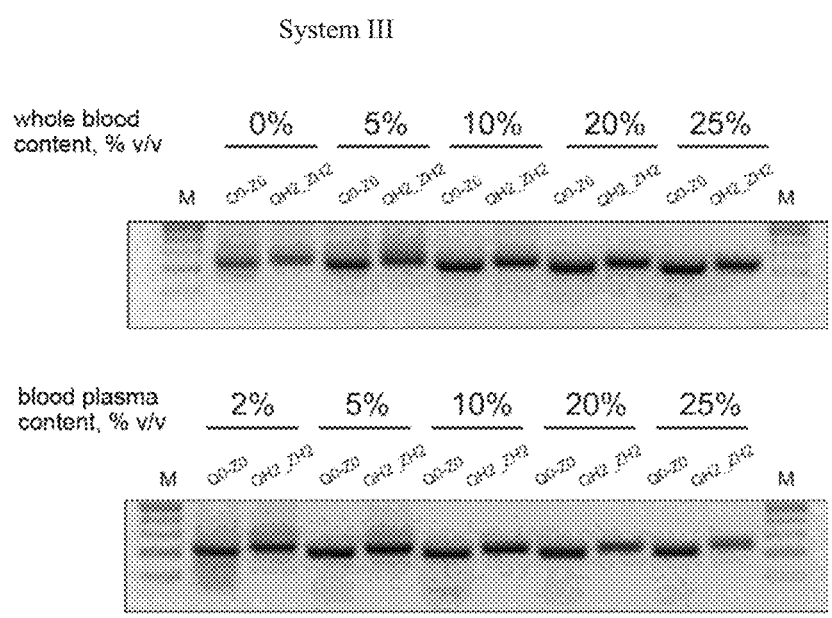
FIG. 12.

| polymerase / primer | MMLV | HIV-p66 | MMLV | HIV-p66 | MMLV | HIV-p66 | MMLV | HIV-p66 |
|---|---|---|---|---|---|---|---|---|
| P0 | 31.3 | | 31.2 | | 31.4 | | 31.2 | |
| P7 | 31.6 | | 31.4 | | 31.4 | | 31.3 | |
| P9 | 31.0 | | 31.1 | | 31.3 | | 31.1 | |
| P11 | 31.3 | | 31.1 | | 31.2 | | 31.1 | |
| P13 | 31.1 | | 31.1 | | 31.2 | | 31.2 | |
| P15 | 31.9 | | 31.8 | | 31.7 | | 31.4 | |
| P17 | 31.2/28.9 | 36.5 | 31.1/28.8 | 36.3 | 31.3/28.8 | 37.3 | 31.3/28.5 | 36.2 |
| P21 | /29.0 | 38.8 | /28.8 | 39.0 | /28.9 | 38.4 | /28.6 | 42.1 |
| P22 | /29.2 | 37.7 | /29.0 | 38.8 | /29.0 | 40.6 | /28.8 | 36.8 |
| P23 | /28.8 | 38.6 | /28.9 | 39.5 | /29.0 | 38.1 | /28.7 | 38.0 |
| P24 | /28.4 | 37.2 | /28.7 | 36.6 | /29.0 | 36.9 | /28.4 | 37.1 |

FIG. 13

A
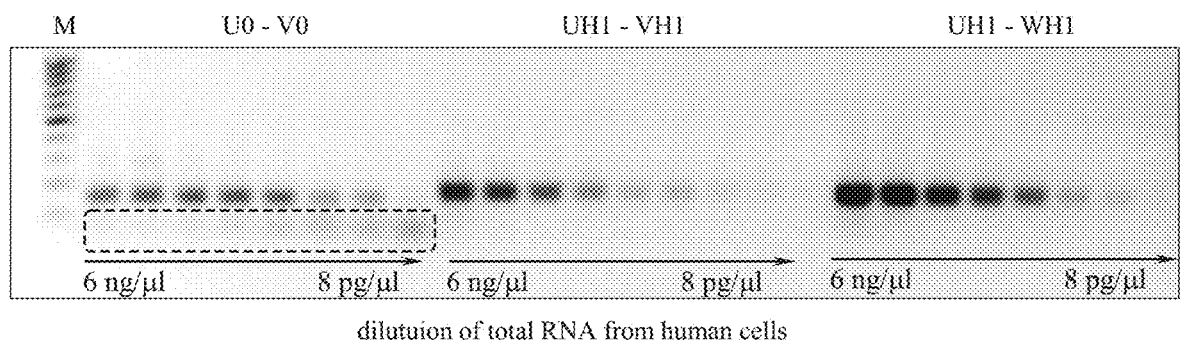
dilutuion of total RNA from human cells
B
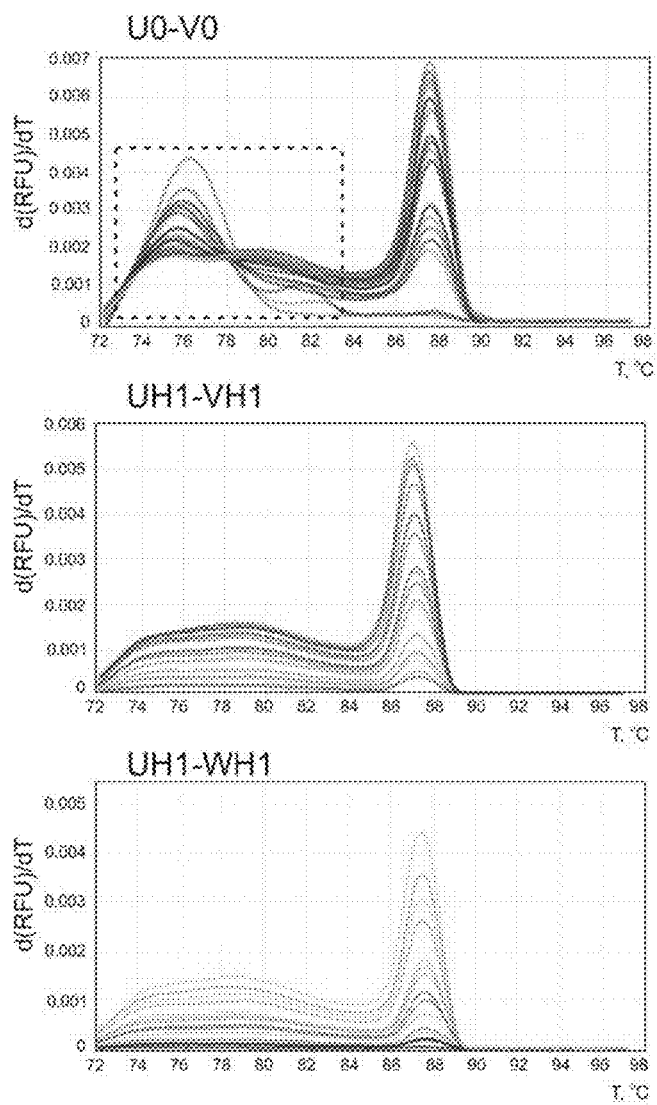
FIG. 14

A

B

| Primer (conditions) | Ct | ΔCt | Amplification factor * |
|---|---|---|---|
| D0 | 29.46 | 3.24 | 9.4 |
| D2 | 24.75 | 7.95 | 247.3 |
| D3 | 27.8 | 4.9 | 29.9 |
| K- (without primers) | 30.96 | 1.74 | 3.3 |
| Initial conditions | 32.7 | 0 | 1 |

METHOD FOR TEMPLATE-BASED ENZYMATIC DNA SYNTHESIS USING PHOSPHORYL GUANIDINE OLIGONUCLEOTIDES AND REACTION MIXTURES FOR CARRYING OUT THE METHOD

CROSS REFERENCE TO RELATED APPLICATIONS

This nonprovisional application is a continuation of International Application No. PCT/RU2018/050115, which was filed on Sep. 17, 2018, and which claims priority to Russian Patent Application No. 2017140645 which was filed in Russia on Dec. 4, 2017, and which are both herein incorporated by reference.

DESCRIPTION OF THE INVENTION

Field of the Invention

The invention relates to the field of molecular biology and molecular diagnostics. The object of the invention is the use of new derivatives of oligonucleotides, namely phosphoryl guanidines, containing one or more phosphate groups bearing guanidine or substituted guanidine residue on the phosphorus atom as primers in the process of template-based amplification, including polymerase chain reaction (PCR) and PCR in combination with reverse transcription.

Terms and Definitions

Ready-to-use reaction mixtures are pre-prepared mixtures of the components necessary for the nucleic acid amplification stage, usually designed to solve routine research tasks.

Template-based enzymatic DNA synthesis is the process of extension of the primer on the 3' end by sequentially inserting an additional nucleotide unit, which process is catalyzed by DNA polymerase.

A kit is a pre-compiled set of ready-to-use reaction mixtures with a protocol for performing a routine task as part of research experiment or diagnostic analysis. For example, kits for polymerase chain reaction (PCR), reverse transcription, and reverse transcription followed by PCR (RT-PCR) in a single tube are widely used in the field of molecular and medical biology.

A primer is an oligomer consisting of units having partially or fully nucleotide nature, wherein said oligomer contains fragments of the structure that provide recognizing the DNA template by the principle of complementary interaction and initiating of the polymerase reaction catalyzed by DNA polymerase, and is extendable on the 3'-end by at least one additional monomeric unit during enzymatic reaction.

PG oligonucleotides are derivatives of oligonucleotides containing one or more phosphate groups in which guanidine or substituted guanidine residue is introduced on the phosphorus atom.

ABBREVIATIONS AND CONVENTIONS

BSA—bovine serum albumin;
DTT—dithiothreitol;
DNA—deoxyribonucleic acid;
ds—double-stranded;
snRNA—small nuclear RNA;
NA—nucleic acid (DNA or RNA);
RT—reverse transcription;
RT-PCR—PCR in combination with reverse transcription, or reverse transcription followed by PCR;
bp—base pairs (pairs of nucleotides);
PCR—polymerase chain reaction;
revertase—RNA-dependent DNA polymerase;
RNA—ribonucleic acid;
Tris—tris(hydroxymethyl)aminomethane;
PG—phosphoryl guanidine group;
Klenow fragment—a large protein fragment of the bacterial DNA polymerase I from $E.\ coli$ retaining polymerase and 3'-5'-exonuclease activity and losing 5'-3'-exonuclease activity;
Ct—threshold cycle;
GFP—green fluorescent protein;
$k_{eff}$—amplification factor;
LNA—"locked" nucleic acid;
ROX, BHQ2, FAM, TAMRA—fluorescent dyes;
RCA—rolling circle amplification reaction;
SD—standard deviation;
SYBR Green I, SYTO-13—DNA-intercalating fluorescent dyes;
KRAS—proto-oncogene, a member of the Ras protein family.

BACKGROUND OF THE INVENTION

Oligonucleotides are widely used as primers for polymerase chain reaction (PCR), which allows to increase the copy number of a DNA fragment whose boundaries are determined by the nucleotide sequence of primers [1, 2].

The structure of primers largely determines the efficiency of PCR forcing to choose their sequence within the framework of rational design and in strict accordance with the set of established criteria. Most often, native oligodeoxyribonucleotides are used as primers. In addition to standard oligonucleotides, a number of oligonucleotide derivatives were proposed as primers, with modified fragments introduced in order to change the efficiency of PCR. For example, such oligonucleotide derivatives include derivatives containing nucleotide units based on "locked" nucleic acids (LNA) [3] or oligoethylene glycol phosphodiester [4] as part of the so-called "cooperative" primers. In addition, the presence of such modifications significantly affects the melting temperature of the formed complexes between the DNA template and the modified oligonucleotide primer. For example, LNA units increase the melting temperature, while hexaethylene glycol decreases thereof.

In addition to changing the structure of the sugar-phosphate backbone, alternative options that affect the efficiency of PCR are modifications of heterocyclic nitrogen bases [5], introduction of non-nucleotide moieties that increase the stability of primer complexes with amplified DNA [6].

Another way to increase PCR accuracy is to use oligonucleotide derivatives with temporary protection of the 3'-terminal fragment, which protection can be removed under the action of chemical agents or physical stimuli, e.g. light or temperature [7, 8], as primers.

A disadvantage of the above-mentioned types of primers based on oligonucleotide derivatives is the need for preliminary obtaining additional monomeric modifiers, which then is to be used during automated oligonucleotide synthesis.

Fully uncharged oligonucleotide derivatives such as morpholino and peptidyl nucleotides are not used as primers, since their sugar-phosphate backbone is not recognized by enzymes [9] and their synthesis is rather demanding in terms of time and resources.

Partially uncharged oligonucleotides, for example, containing residues of phosphotriesters, that is, bearing a residue of an aliphatic alcohol instead of one of the oxygen atoms, can be used as primers for DNA amplification, however, obtaining thereof requires the use of special phosphoramide nucleotide monomers and non-standard conditions of post-synthetic deblocking and isolation of synthesized oligonucleotides [10]. There is no described example of the widespread use of partially uncharged oligonucleotides in reaction mixtures with different temperature modes of primer extension and DNA fragment amplification using a wide range of DNA polymerases.

The closest analogue to the proposed method, i.e. the prototype, is the method for amplification in the presence of modified oligonucleotide primers containing substituents on the phosphorus atom within the internucleotide phosphate groups introduced instead of the oxygen atom, namely oligonucleotides with phosphorothioate residues [11]. Primers with this type of backbone modification can be prepared using standard nucleotide monomers, but special oxidizing agents. A disadvantage of the prototype is the limited conditions for using such a system, which consist of the following:

phosphorothioate-containing primers are used only for DNA detection;
in the prototype, the set of enzymes used is limited, namely, by polymerase lacking 3'→5' exonuclease activity (i.e., the use of polymerase with corrective activity will not lead to a decrease in non-specific amplification); and able to extend the primer in the range of 55-61° C.;
the conditions for the amplification reaction are thermo-cyclic mode;
the need to introduce a 5'-end tag into the modified oligonucleotide used to detect DNA product.

In contrast, the use of phosphoryl guanidines in enzymatic reactions is efficient due to the properties of this class of compounds, in connection with the following:

their synthesis does not require the introduction of additional amidophosphite monomers of the precursors in the synthetic protocol and is carried out on standard automated DNA/RNA synthesizer;
the number and position of phosphoryl guanidine groups (PG) in the oligonucleotide is not limited, and is set and controlled by automated synthesis, which allows to obtain both fully modified derivatives and derivatives with partially substituted phosphodiester residues;
the presence of PG does not lead to a significant change in the melting temperature of NA/NA complexes under conditions of moderate ionic strength of the solutions;
the introduction of guanidine group (at least eight atoms) instead of one of the oxygen atoms (negatively charged under physiological conditions) significantly increases the volume of the substituent on the phosphorus atom and makes the PG uncharged under physiological conditions, as shown in Example 1 of the present description;
the introduction of PG into the oligonucleotide provides said oligonucleotide with the chemical stability in a wide pH range and resistance to the action of nucleases;
by changing the position and number of phosphoryl guanidine groups, it is possible to obtain oligonucleotides with a wide range of physicochemical properties having the same nucleotide sequence.

SUMMARY OF THE INVENTION

A key difference of the present invention from the analogues is the introduction of one or more phosphoryl guanidine moieties into the structure of oligonucleotide primer. The introduction of a guanidine group instead of one of the oxygen atoms significantly increases the volume of the substituent on the phosphorus atom and makes the phosphoryl guanidine derivatives of oligonucleotides uncharged under physiological conditions. The presence of a bulky and neutral charge group on the phosphorus atom in the phosphoryl guanidine derivatives of oligonucleotides leads to a change in substrate properties thereof as primers for template-based enzymatic DNA synthesis. At the initial stages of the reaction, the phosphoryl guanidine moiety in the primer structure perturbs the structure of the primer-template complex of the polymerase with DNA or RNA substrate, changing the efficiency of the enzyme action. As a result, the use of primers having phosphoryl guanidine moiety affects the final yield, composition or rate of accumulation of reaction products of template-based enzymatic DNA synthesis. In particular, the sensitivity of the reaction and the specificity of the accumulation of the target product can be increased by using phosphoryl guanidine derivatives of oligonucleotides in PCR. Thus, the phosphoryl guanidine moieties used in the primers to initialize the template-based enzymatic synthesis provide significant differences from said analogues, for example, phosphorothioate-containing oligonucleotides.

The technical result of the claimed invention is increasing the reliability, sensitivity and specificity of the detection of the analyzed nucleic acid sequences, and also simplifying the method for template-based DNA synthesis.

The technical result is achieved by the fact that a primer containing at least one inter-unit phosphoryl guanidine group is used for the template-based enzymatic synthesis of nucleic acids. The general structure of the primer is shown in FIG. 1A, where Z is phosphoryl guanidine group.

In specific applications, template-based enzymatic DNA synthesis by the method described above can be used to amplify nucleic acids using both DNA and RNA as the primary template. The method can be implemented both in thermo-cyclic and isothermal protocols, in particular, in the process of amplification by the rolling circle mechanism. Application of the proposed PCR method to research and diagnostic purposes seems to be in the most demand. In particular, the use of the method for the detection of single nucleotide mutations using allele-specific PCR can increase the sensitivity and specificity of the method. Enzymatic DNA synthesis using phosphoryl guanidine oligonucleotides in reverse transcription reactions both independently and in combination with subsequent PCR seems to be equally in demand.

In normal laboratory practice, the routine protocols are often implemented using commercially available ready-to-use reaction mixtures and sets of such mixtures with instructions for carrying out the experiment stage-by-stage to achieve the desired result. Template-based enzymatic DNA synthesis according to the above-described method can present the main stage or be an integral part of a more complex protocol for conducting an experiment for research or medical diagnostic purposes.

Thus, the present invention discloses the use of phosphoryl guanidine oligonucleotides that meet the above-described criteria to create improved systems for detection and quantification of nucleic acids based on PCR and RT-PCR.

BRIEF DESCRIPTION OF THE DRAWINGS

The claimed invention is illustrated by the following figures:

FIG. 1 and FIG. 2 represent a description of the compounds used in the Examples. FIG. 1 shows the structure of the primer and uncharged phosphoryl guanidine group (Z) in general form (A); examples of used phosphoryl guanidine groups (B) bearing guanidine residue (g"), N,N,N',N'-tetramethylguanidine (g'), 1,3-dimethylimidazolidin-2-imine (g), N,N'-bis(tetramethylene)guanidine (g'''). FIG. 2 shows the sequence and structure of the oligonucleotides used in the examples of the invention, where g", g, g is a phosphoryl guanidine group, [$^{32}$P] is a radioactive label, * is a fluorescent label (FAM or TAMRA).

FIG. 3 illustrates the model systems used in the examples of the invention in which PG oligonucleotides act as primers (A) or templates (B), where g is phosphoryl guanidine group.

FIG. 4 illustrates an example of the use of an oligonucleotide phosphoryl guanidine derivative as a primer in a reaction catalyzed by a thermostable DNA-dependent DNA polymerase in thermo-cyclic (1) and isothermal (2) modes. The figure presents the result of electrophoretic analysis of the $M_{30}$/Z complex (the system is shown in FIG. 3A) in the presence of Taq DNA polymerase in thermo-cyclic mode (A); the degree of accumulation of the full-size product of the reaction in the M/T complex (the system is shown in FIG. 3A) in the presence of Taq DNA polymerase in isothermal mode; primer sequences Z0÷ZF and T0÷T3 are shown in FIG. 2.

FIG. 10 demonstrates the ability of phosphoryl guanidine derivatives of oligonucleotides to reduce the likelihood of accumulation of the non-specific products of PCR catalyzed by Taq DNA polymerase, including in combination with "hot start" technology. The figure presents the result of electrophoretic analysis of PCR catalyzed by Taq-DNA polymerase in the presence of the corresponding primer pairs under standard conditions (A) and under the condition of delayed "hot" start (B), the curves of thermal denaturation of amplification products of the eGFP gene fragment (C), where M is a marker of DNA lengths from 100 to 400 bp; primer sequences are shown in FIG. 2. The melting region of non-specific products is indicated by a dotted line.

FIG. 12 shows the efficiency of the use of phosphoryl guanidine derivatives of oligonucleotides as primers for DNA-dependent DNA polymerases used in commercial PCR systems, including DNA determining in human body fluids: whole blood and blood plasma. The figure presents the result of electrophoretic analysis of PCR in system I (DNA-dependent DNA polymerase Pfu) and II (a mixture of DNA-dependent DNA polymerases Pfu and Taq) (panel A), system III (commercial system for PCR in whole body fluids) (panel B) using a pair of standard primers (Q0-Z0) and a pair of phosphoryl guanidine derivatives. M is a marker of DNA lengths from 100 to 500 bp; primer sequences are shown in FIG. 2.

FIG. 13 illustrates the possibility of the use of phosphoryl guanidine derivatives of oligonucleotides as primers for RNA-dependent DNA polymerases (revertases). The figure presents the values of the threshold cycle of amplification reactions after reverse transcription using RNA-dependent DNA polymerases MMLV and HIV-p66 in the presence of intercalating dyes SYBR and SYTO-13 (highlighted in color), primer sequences are shown in FIG. 2

FIG. 14 shows the possibility and advantages of the use of phosphoryl guanidine derivatives of oligonucleotides as primers in one-step RT-PCR systems. The figure presents the result of electrophoretic analysis (A) and thermal denaturation curves (B) of the products of RT products followed by PCR using a pair of standard primers (U0-V0) and pairs of phosphoryl guanidine derivatives (UH1-VH1; UH1-WH1) specific to the U12 sequence of human snRNA in the total RNA of human cells. M is a marker of DNA lengths from 100 to 400 bp; primer sequences are shown in FIG. 2, the region of the mobility of non-specific products is indicated by a dotted line.

DETAILED DESCRIPTION OF THE INVENTION

Figure 5:
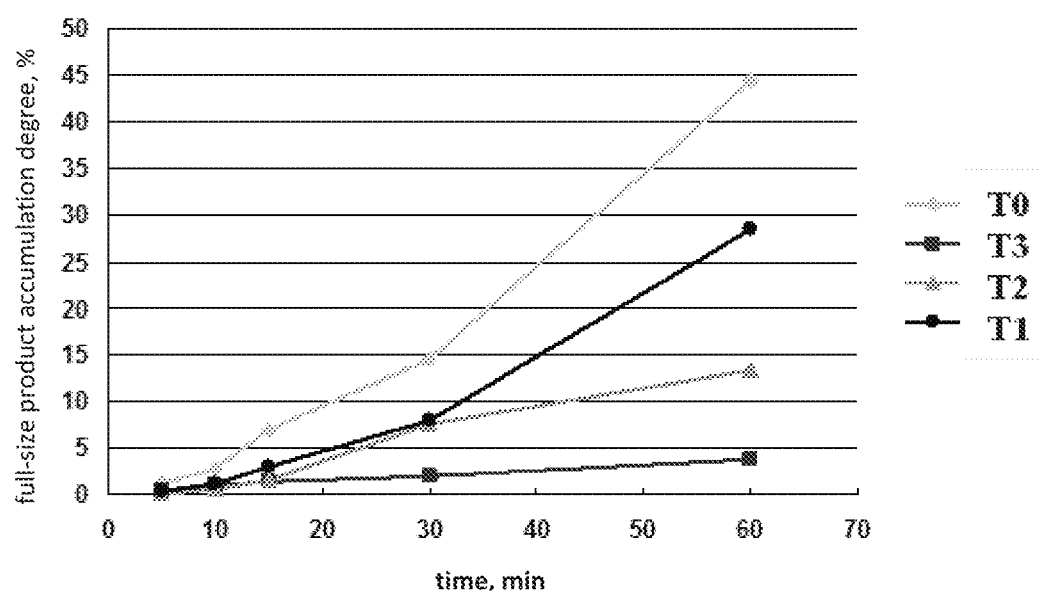
FIG. 5 illustrates an example of the use of an oligonucleotide phosphoryl guanidine derivative as a primer in a reaction catalyzed by a mesophilic DNA-dependent DNA polymerase. The degree of accumulation of the full-size product of the reaction in the $M_{40}$/T complex (the system is shown in FIG. 3A) in the presence of T5 phage DNA polymerase; primer sequences T0→T3 are shown in FIG. 2.

The use of modified oligonucleotides in enzymatic reactions of template-based synthesis of nucleic acids can be accompanied by various effects that affect the overall yield of the reaction. Most of the known chemical modifications of oligonucleotide primers lead to disruption of the interaction of nucleic acid substrates with enzymes. In this context, completely uncharged derivatives of oligonucleotides were never used as primers, since it was obvious from the literature that their carbohydrate-phosphate backbone will not be recognized by enzymes [9].

The invention describes the possibilities of the use of primers with phosphoryl guanidine moieties in template-based enzymatic DNA synthesis systems. In comparison with analogs, the method for template-based enzymatic DNA synthesis using primers containing phosphoryl guanidine moieties [12-14] combines a number of advantages disclosed in the invention, the combination of which ensures the achievement of the technical result.

The general structure of a phosphoryl guanidine group (Z) containing primer is shown in FIG. 1A, where each of the substituents R1, R2, R3, and R4 may be a hydrogen atom H or an optionally substituted organic radical. Each of the substituents R1, R2, R3, and R4 is independently selected from the group comprising H, C1-10 alkyl, C2-10 alkenyl, C2-10 alkynyl, -C6-10 aryl or -C5-10 heteroaryl (for example, FIG. 1A, g", g'); where each alkyl, alkenyl, alkynyl, aryl, heteroaryl, alkylene or heteroalkylene may be further substituted; and additionally R1 and R2, together with the atom to which they are bonded, form a 5-8 membered heterocycle; in some applications, R1 and R2, together with the atom to which they are bonded, form a 5-8 membered heterocycle, preferably pyrrolidine, piperidine, piperazine, morpholine, since the size of such substituents should not exclude the interaction of PG oligonucleotides with the enzyme necessary for initiation of template-based synthesis reaction. Preferably, R1 and R2, together with the atom to which they are bonded, form a 5-membered heterocycle, for example pyrrolidine (FIG. 1, g'"). In some applications, R2 and R3 together form an alkylene or heteroalkylene chain of 2-4 atoms, and R1 and R4 are each independently selected from the group comprising H and C1-4 alkyl. In some applications, R2 and R3 together form a CH2-CH2 chain, and R1 and R4 are —H or methyl (for example, FIG. 1, g). Part of the preferred compounds encompassed by the present invention correspond to the PG formulas bearing the guanidine (g"), N,N,N',N'-tetramethylguanidine (g'), 1,3-dimethylimidazolidin-2-imine (g), or N,N'-bis(tetramethylene)guanidine (g'") residues shown in FIG. 1B.

FIG. 1. The structure of primer and uncharged phosphoryl guanidine group (Z) in general form (A); examples of used phosphoryl guanidine groups (B) bearing the guanidine (g"), N,N,N',N'-tetramethylguanidine (g'), 1,3-dimethylimidazolidin-2-imine (g), or N,N'-bis(tetramethylene)guanidine (g'") residues.

The algorithm for construction of PG-modified primer involves the introduction of at least one phosphoryl guanidine moiety into the oligonucleotide and allows the use of completely uncharged phosphoryl guanidine derivatives of oligonucleotides as primers (FIG. 2). However, the presence of the phosphoryl guanidine moiety in the primer does not preclude the introduction of additional functional groups that provide additional properties to the primers and final product. For example, for further detection of the reaction products of template-based DNA synthesis, the possibility of introduction of fluorescent and radioactive labels into PG-modified primers is presented.

One of the key properties and selection criteria for (any) modified oligonucleotides used as primers is their ability to form a competent primer-template complex to initiate the reaction and the ability to act as a template for the synthesis of the 3'-end region of the complementary strand (when the nucleotide sequence of the initial primer acts as the template). The replacement of negatively charged inter-unit phosphate groups with neutral groups, as well as the change in the volume of substituents on the phosphorus atom, should affect the ability of the oligonucleotide to interact with the DNA and RNA template and be extended by DNA- or RNA-dependent DNA polymerases. The invention contains a description of examples demonstrating the ability of oligonucleotides containing phosphoryl guanidine moieties both to act as primers and to provide properties of the template in the process of extension of the complementary strand. Various applications of template-based DNA synthesis, in particular, DNA amplification in molecular diagnostics, biotechnology and genetic engineering, suggest the use of a wide range of DNA polymerases. It was shown that phosphoryl guanidines act as substrates for a wide range of both mesophilic and thermophilic DNA-dependent DNA polymerases, regardless of the presence of 3'→5'/5'→3' exonuclease activity under the conditions of thermo-cyclic and isothermal modes (Example 2, 3, 4, 5, 6, 10, 13), as well as RNA-dependent DNA polymerases (Example 11, 12).

The presented invention illustrates the possibility of the use of primers with phosphoryl guanidine moieties at various temperatures (temperature protocols) for polymerase (enzymatic) reactions. The described property of the new class of primers can be used in the development of systems for synthesis and diagnostics based on different protocols for the detection and quantification of nucleic acids.

The use of PG-modified primers for amplification of DNA in the PCR reaction, as well as RNA in the reverse transcription reaction with subsequent PCR, seems to be the most demanded. The results obtained using primers with a pre-selected number and position of phosphoryl guanidine moieties demonstrate increased specificity and sensitivity by reducing the yield of non-specific products of the reaction. A key feature that improves the quality of the results of qualitative and quantitative determination of nucleic acids by PCR and RT-PCR with primers containing phosphoryl guanidine moieties is a decrease in the yield of short non-specific products, often classified as "primer-dimers".

(Example 8, 10, 12). The described property will reduce the level of sensitivity and reliability of the quantification of nucleic acids. Reducing the yield of by-products can also be achieved by combining the use of primers with phosphoryl guanidine moieties with already known solutions aimed at modifying other components of the reaction mixture, for example, "hot start" technologies. When used in PCR, phosphoryl guanidines are able to change the amplification factor. Depending on the location, number and frequency of PG-modified monomers, the amplification efficiency can be comparable to the standard reaction with unmodified primers or can be significantly reduced, up to complete elimination of the amplification. The influence on the amplification efficiency can be due to the participation of modified monomers in two main stages, which are initiation of the polymerization reaction and extension of the complementary strand, when the primer nucleotide sequence acts as a template. When selecting the position and number of modified monomers that allow only a slight (within 10-15%) decrease in the amplification efficiency, the use of primers with phosphoryl guanidine moieties will not require a change in the amplification protocol, in particular PCR and RT-PCR, when switching from standard (unmodified) primers for solving particular problems. In addition, the examples demonstrate the possibility of simultaneous use of PG-modified and standard primers in enzymatic reactions (FIG. 10, Example 8). It was also shown that template-based enzymatic synthesis using primers containing phosphoryl guanidine moieties can be successfully implemented in protocols of isothermal amplification of DNA by the "rolling circle" mechanism. The use of PG-modified primers in allele-specific PCR allows to increase the reliability of the detection of single nucleotide mutations in the genome.

Using sequencing by the method of Sanger, it was shown that the presence of phosphoryl guanidine moieties does not cause the formation of mutations due to the interaction of the enzyme with modified monomers. This property provides the applicability of PG-modified primers for solving research and practical problems associated with the amplification of nucleic acids, construction of pre-defined sequences and determination of their primary structure.

The control of the synthesis of the 3'-terminal region of one of the strands, in particular the formation of "sticky" ends, is of interest for solving a number of genetic engineering tasks in the construction of artificial DNA molecules with a given nucleotide sequence. For example, "sticky"-end PCR products can be used in the construction of expression plasmid DNA vectors. The present invention demonstrates the possibility of both obtaining a full-size complementary strand and preventing the synthesis of portion of the 3'-terminal units.

An important parameter in choosing the components of amplification systems is the possibility of carrying out a reaction using various objects as a template, for example, synthetic nucleic acids, plasmid DNAs, total RNA, and genomic DNA of cells and tissues, viral nucleic acids, as well as whole body fluids (for example, blood and blood plasma) that are needed in the diagnosis of human and animal diseases. In the examples illustrating the invention, the successful use of PG-modified primers with different variants of the templates is presented, which provides possibilities of widespread implementation of the obtained technical result.

Often, commercially available ready-to-use reaction mixtures are included in laboratory practice to solve routine tasks; moreover, complex stage-by-stage manipulations are usually carried out using sets of reagents containing the necessary components and instructions for conducting an experiment and achieving a scientific or diagnostic result. For practical purposes, the method for template-based enzymatic DNA synthesis using primers with phosphoryl guanidine moieties can be implemented using ready-to-use reaction mixtures and sets of reagents or reaction mixtures for the detection and amplification of nucleic acids, which are in demand for solving both research and diagnostic tasks. Moreover, the stages of amplification of nucleic acids using phosphoryl guanidine derivatives of oligonucleotides can become a part of more complex protocols and sets of reagents for their implementation, for example, the preparation of DNA libraries for differential analysis of gene expression using high-performance methods. The use of the proposed method can not only improve the result of a specific stage of template-based DNA synthesis, but also, in individual applications, will eliminate some stages, for example, intermediate purification from non-specific by-products.

The invention is illustrated in more detail below by the following examples of specific implementation, which do not limit the scope of the invention. Numerous embodiments of the invention within the scope of the claims of the invention that arise from the examples should be apparent to those skilled in the art based on the description above and the following examples. A person skilled in the art will determine the suitability of a particular group or combination of groups and location in the oligonucleotides used as primers in the template-based DNA synthesis reactions empirically and independently.

Example 1. Description of the Systems Used Below

PG oligonucleotides and unmodified oligodeoxyribonucleotides are shown in FIG. 2. Oligonucleotides contained from 8 to 40 nucleotide units. Phosphoryl guanidine groups (PG) are presented as unmodified (g"), branched (g'), locked (g) residue and guanidine residue with bulky substituents (g''') (FIG. 1B). The number of PG in the oligonucleotides ranged from single group to 100% (FIG. 2).

PG oligonucleotides acted as primer oligonucleotides (FIG. 3A) or templates (FIG. 3B), contained a fluorescent (*-FAM or TAMRA) or radioactive label ([$^{32}$P]).

Native and PG oligonucleotides (FIG. 2), plasmid DNA containing the eGFP gene; human whole blood and blood plasma preparations containing previously added plasmid DNA; Hepatitis C virus RNA (HCV); total RNA of human breast adenocarcinoma cells MCF-7; plasmid pUC19; human genomic DNA were used as templates.

Mesophilic and thermophilic enzymes with and without 3'→5'/5'→3' exonuclease activity were used as DNA polymerases: Taq DNA polymerase, T5 phage DNA polymerase, E. coli DNA polymerase I (Klenow fragment), DNA polymerase Pfu, RNA-dependent DNA polymerases (revertases) MMLV and HIV-p66; DNA polymerase phi29.

Example 2. PG Oligonucleotide as a Primer in the Reaction Catalyzed by Thermostable Polymerase in Thermo-Cyclic (1) and Isothermal (2) Modes (1) To demonstrate the use of PG oligonucleotides as primers (the system is shown in FIG. 3A), the reaction mixtures (10 µl) contained: native oligonucleotide $M_{30}$ (10 µM); unmodified oligonucleotide Z or PG oligonucleotide Z1÷ZH1 (10 µM, primer sequences Z0÷ZF are shown in FIG. 2); set of triphosphates (0.1 mM each) dATP, dCTP, dGTP, and fluorescently labeled dUTP (fluorescein-6-aminothiocarbonyl-[5-(3-aminoallyl)-2'-deoxyuridine-5'-triphosphate]); 1.8 mM $MgCl_2$, Tris-HCl (10 mM) pH 8.8, KCl (50 mM); 0.1% Tween-20, Taq DNA polymerase (2 units of activity). The reaction was carried out in thermo-cyclic mode: 95° C. for 10 seconds, 61° C. for 10 seconds, 72° C. for 30 seconds (32 cycles). After 25 minutes, the reaction was stopped by adding a 2% solution of lithium perchlorate in acetone. All samples were separated by electrophoretic analysis in a 20% denaturing polyacrylamide gel, the result of electrophoretic analysis was recorded using a fluorescence scanner (FIG. 4A). The efficiency of extension of PG oligonucleotides on the DNA template (lanes Z1-ZF in FIG. 4A) was compared with that for the native oligonucleotide Z0 (lane Z0 in FIG. 4A).

(2) To demonstrate the use of PG oligonucleotides as primers (the system is shown in FIG. 3A), reaction mixtures (10 µl) contained: native oligonucleotide $M_{40}$ (30 µM), radioactive labeled oligonucleotide T0÷T3 (10 µM, primer sequences T0÷T3 are shown in FIG. 2); set of triphosphates (0.2 mM each), 1.8 mM $MgCl_2$, Tris-HCl (10 mM) pH 8.8, KCl (50 mM); 0.1% Tween-20, Taq DNA polymerase (1 unit of activity). The reaction was carried out in isothermal mode (FIG. 4B) for 20-120 minutes at 37° C. and was stopped by the addition of a 2% solution of lithium perchlorate in acetone. All samples were separated by electrophoretic analysis in a 15% denaturing polyacrylamide gel. The degree of accumulation of the full-size product of the reaction was calculated as the ratio of the intensity in the band corresponding to the reaction product to the total intensity of all the bands in the lane. The relative error of determination in all experiments did not exceed 15% (FIG. 4B).

It was seen (FIG. 4A) that PG oligonucleotides are able to act as primers in the presence of thermostable Taq DNA polymerase and, under the conditions of the thermo-cyclic temperature mode, to extend the full-size product, as the native oligonucleotide primer Z0 does. A decrease in the efficiency of extension was observed for oligonucleotide Z1,2, which contains two consecutive PGs close to the 3' end. Under isothermal conditions (FIG. 4B), a similar result was observed: the degree of accumulation of the full-size product of the reaction for oligonucleotides T1 and T2 was close to that for T0. A decrease in the degree of accumulation of the full-size product of the reaction was observed for oligonucleotide T3 containing PG close to the 3' end.

Example 3. PG Oligonucleotide as a Primer in the Reaction Catalyzed by Mesophilic Polymerase To demonstrate the use of PG oligonucleotides as primers (the system is shown in FIG. 3A), the reaction mixtures (5 µl) contained: native oligonucleotide M40 (30 µM), radioactive labeled oligonucleotide T0-T3 (10 µM, primer sequences T0-T3 are shown in FIG. 2); set of triphosphates (0.2 mM each), $MgCl_2$ (20 mM), Tris-HCl (50 mM) pH 8.0, NaCl (100 µM), DTT (5 mM), 0.1 mg/m BSA; T5 phage DNA polymerase (500 µM). The reaction was carried out for 6-60 minutes and was stopped by the addition of a solution used for applying samples for electrophoresis, which contained 7 mM EDTA. All samples were separated and analyzed analogously to Example 2 (2). The relative error of determination in all experiments did not exceed 15% (FIG. 5).

It was seen (FIG. 5) that all PG oligonucleotides were able to act as primers in the presence of mesophilic T5 phage DNA polymerase in isothermal mode, although the efficiency of PG oligonucleotides extension to the full-size product was less than in the case of the native oligonucleotide T0.

Example 4. PG Oligonucleotide as a Template in the Reaction Catalyzed by Thermostable Polymerase To demonstrate the use of PG oligonucleotides as templates (the system is shown in FIG. 3B), the reaction mixtures (10 µl) contained: unmodified oligonucleotide Z or PG oligonucleotide Z1÷ZF (10 µM, primer sequences Z0÷ZF are shown in FIG. 2), fluorescently labeled native primer FAM-$N_8$ (10 µM, sequence shown in FIG. 2), complete set of dNTP triphosphates (10 mM), Taq DNA polymerase (2 units of activity), 1.8 mM $MgCl_2$, Tris-HCl (10 mM) pH 8.8, KCl (50 mM); 0.1% Tween-20. The reaction was carried out in thermo-cyclic mode: 95° C. for 10 seconds, 61° C. for 10 seconds, 72° C. for 30 seconds (32 cycles). The reaction was stopped and analyzed analogously to Example 2 (1).

Figure 6:
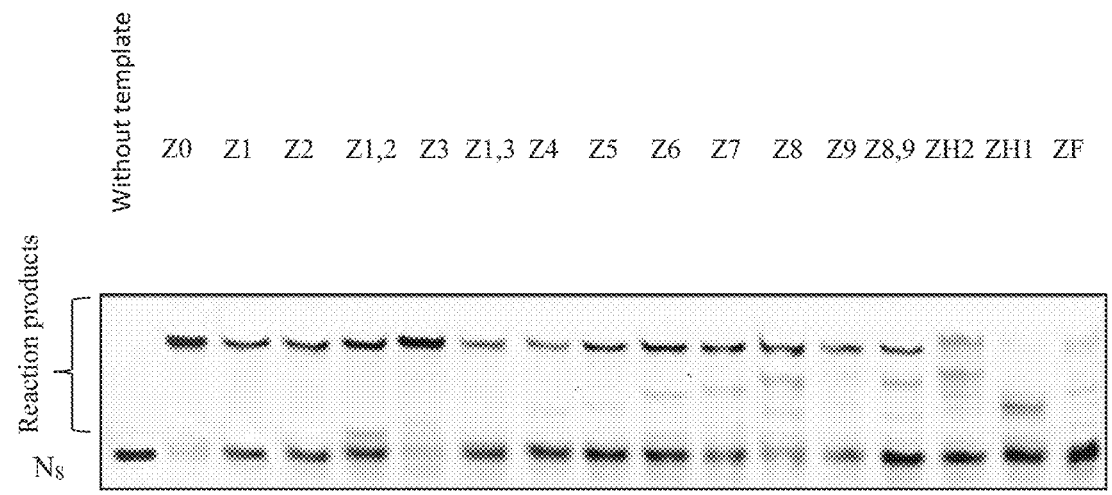
FIG. 6 illustrates the ability of phosphoryl guanidine derivatives of oligonucleotides to act as a template in a reaction catalyzed by a thermostable DNA-dependent DNA polymerase. The figure shows the result of electrophoretic analysis of the Z/$N_8$ complex (the system is shown in FIG. 3B) in the presence of Taq DNA polymerase; primer sequences Z0÷ZF are shown in FIG. 2.

It was seen (FIG. 6) that all PG oligonucleotides were able to act as templates in the presence of thermostable Taq DNA polymerase in thermo-cyclic mode. The efficiency of extension of the native oligonucleotide to the full-size product increased with the increasing a distance between the PG and 3' end of the PG-oligonucleotide. The PG oligonucleotide containing consecutive (ZH1) or alternating modified PG (ZH2, ZF) exerted maximum influence on the yield of the full-size product.

Example 5. PG Oligonucleotides as a Template in the Reaction Catalyzed by Mesophilic Polymerase To demonstrate the use of PG oligonucleotides as templates (the system is shown in FIG. 3B), reaction mixtures (10 µl) contained: 10 µM of unmodified oligonucleotide Z0 or PG oligonucleotide Z1-ZF (primer sequences Z0-ZF are shown in FIG. 2), 10 µM of TAMRA-labeled native primer *$N_8$ (FIG. 2), complete set of dNTP triphosphates (10 mM), Klenow fragment (2 units of activity), Tris-HCl (50 mM), pH 7.6, $MgCl_2$ (10 mM), DTT (5 mM). The reaction was carried out for 30 minutes in isothermal mode at 37° C. The reaction was stopped and analyzed analogously to Example 2.

Figure 7:
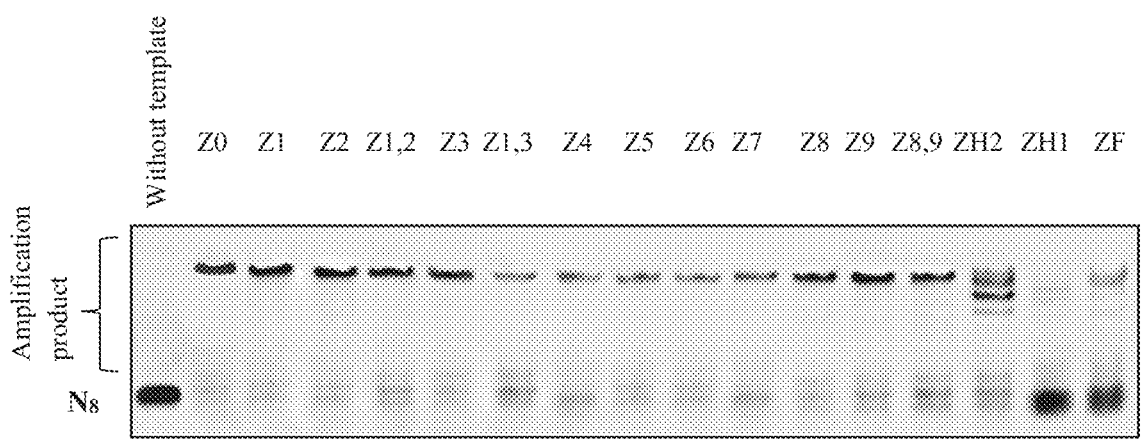
FIG. 7 illustrates the ability of phosphoryl guanidine derivatives of oligonucleotides to act as a template in a reaction catalyzed by a mesophilic DNA-dependent DNA polymerase. The result of electrophoretic analysis of the Z/$N_8$ complex (the system is shown in FIG. 3B) in the presence of Klenow fragment, primer sequences Z0÷ZF are shown in FIG. 2.

It was found (FIG. 7) that all PG oligonucleotides were able to act as templates in the presence of a mesophilic polymerase, i.e. the Klenow fragment, in isothermal mode. The efficiency of extension of the native oligonucleotides to the full-size product increased with the increasing a distance between the PG and 3' end of the native oligonucleotide. The PG oligonucleotide ZH1 containing consecutive phosphoryl guanidine groups exerted the maximum influence on the yield of the full-size product.

Example 6. PCR Efficiency Using PG Oligodeoxyribonucleotides as Primers

Amplification of the eGFP gene fragment was carried out in a reaction buffer containing 50 mM Tris-HC, pH 8.5, 50 mM KCl, 0.2 mM of each deoxynucleoside triphosphate, 2 mM $MgCl_2$, 0.03 units of activity/µl Taq DNA polymerase.

Amplification mode was 95° C. for 5 min, 47 cycles: 95° C. for 10 seconds, 61° C. for 10 seconds, 72° C. for 10 seconds.

A 10-fold serial dilution of plasmid DNA containing the eGFP gene from $10^{-9}$ g to $10^{-17}$ g was used a template.

Figures 8, 9:
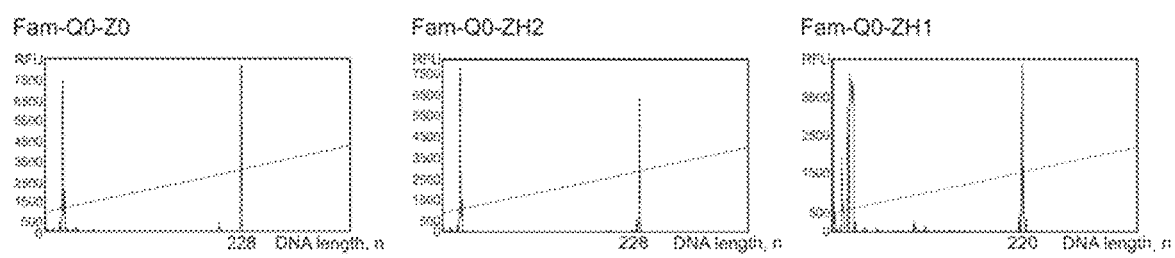
FIG. 8 shows changes in PCR efficiency when using phosphoryl guanidine derivatives of oligonucleotides as primers. The table in the figure presents the amplification factors in the system of primer pairs, wherein one of the oligonucleotides contains at least one phosphoryl guanidine moiety, in comparison with the standard primer system (Q0-Z0). The primer sequences are shown in FIG. 2. The values of the PCR efficiency factors obtained from the results of three or more independent experiments are given. SD is the standard deviation.
FIG. 9 illustrates the possibility to control the length of a growing complementary DNA strand using phosphoryl guanidine moieties in the initial primer. The figure presents the result of analysis of the length of the PCR products of the eGFP gene fragment in the presence of the corresponding primer pairs (captions of diagrams: Q0-Z0—a pair of primers without modifications; Q0-ZH2 and Q0-ZH1—pairs of unmodified primer with phosphoryl guanidine derivatives of oligonucleotides) by fragment analysis performed in an automated capillary analyzer, where * is the FAM fluorescent label, primer sequences Q0, Z0, ZH1, and ZH2 are shown in FIG. 2.

The pairs shown in FIG. 8, which are based on standard native oligonucleotides and PG oligonucleotides, were used as primers (forward+reverse). PG oligonucleotides differed in the number and location of phosphoryl guanidine units in the oligonucleotide strand. Oligonucleotide sequences are shown in FIG. 2. The concentration of each primer was 500 nM.

The amplification efficiency was determined by real-time PCR in the presence of intercalating dye SYBR Green I on a LightCycler 96 instrument (Roche, Switzerland).

The amplification efficiency was compared based on the amplification factor values ($k_{eff}$), using the approach of the linearizing coordinates of the dependence $C_t$ (lg $C_0$) (where $C_t$ is the threshold cycle, $C_0$ is the initial concentration of the template) implemented in the program LightCycler 96 Software version 1.1.0.1320. The amplification factor values are shown in FIG. 8 (the values of PCR efficiency factors obtained from three or more independent experiments are given; SD is the standard deviation). It was seen that single PG in the primer structure (see primers Z1÷Z9) did not significantly affect the amplification efficiency. The influence of phosphoryl guanidine groups was determined by their location in the primer strand. Consecutively positioned PGs (primer ZH1) significantly reduced $k_{eff}$, i.e. to 1.44. The introduction of modifications into the "next-but-one" positions (alternating modified phosphoryl guanidine units) ensured the accumulation of the full-size product.

Example 7. Determination of the Length of the Growing DNA Strand

The amplification of the eGFP gene fragment was carried out in the reaction buffer as described previously in Example 6.

Amplification mode was 95° C. for 5 min, 28 cycles: 95° C. for 10 seconds, 61° C. for 10 seconds, 72° C. for 10 seconds.

Plasmid DNA containing the eGFP gene in an amount of $10^{-10}$ g per reaction was used as a template.

The pairs (*Q0-Z0), (*Q0-ZH1), (*Q0-ZH2), where * is the fluorescent FAM label, were used as primers. PG oligonucleotide sequences are shown in FIG. 2. The concentration of each primer was 500 nM.

Determining the exact length of PCR products using fragment analysis was performed in an automated capillary analyzer. The data presented in FIG. 9 show that the use of oligonucleotides Z0 and ZH2 allowed to obtain full-size PCR products with a length of 228 bp. At the same time, the use of oligonucleotide ZH1 led to the termination of the synthesis of a complementary strand 8 nucleotides before the 5' end, which led to the formation of DNA molecules with "sticky" ends.

Example 8. Comparison of the Accumulation of Specific and Non-Specific Products of PCR Catalyzed by Taq-DNA Polymerase Using Standard and PG-Modified Oligodeoxyribonucleotides as Primers The amplification of the eGFP gene fragment was carried out in the reaction buffer as described previously in Example 6.

The amplification mode is described previously in Example 7.

The template used is described previously in Example 6.
Pairs of standard native oligonucleotides (Q0-Z0), modified PG oligonucleotides (QH2-ZH2), standard and modified oligonucleotides (QH2-Z0), and a mixture of three oligonucleotides (Z0-QH2/Q0, the last ones in a ratio of 50/50%) were used as primers (forward-reverse). Oligonucleotide sequences are shown in FIG. 2. The concentration of primers was 500 nM.

The analysis of PCR products was carried out by agarose gel electrophoresis (FIGS. 10A and B, M is a marker of DNA lengths from 100 to 400 bp) and by thermal denaturation of PCR products in an iQ5 instrument (Bio-Rad, USA) in the presence of an intercalating dye SYBR Green I (FIG. 10B).

It was seen (FIGS. 10A and B) that the use of the pair of modified PG oligonucleotides (QH2-ZH2) increased the reliability and allowed to significantly reduce the formation of non-specific products compared to using both native oligonucleotides (Q0-Z0) and mixtures of native and modified oligonucleotides (QH2-Z0) and (Z0-QH2/Q0).

The complete absence of non-specific products was achieved using PCR systems with deferred "hot" start on modified PG oligonucleotide primers compared with native primers (FIG. 10B).

Example 9. Analysis of Mutations in the Growing DNA Strand

The amplification of the eGFP gene fragment was carried out in the reaction buffer as described previously in Example 6.

The amplification mode is described previously in Example 7.

The template used is described previously in Example 6.

The pairs (Q0-Z0), (Q0-ZH1), (QH2-ZH2) were used as primers (forward-reverse). Oligonucleotide sequences are shown in FIG. 2.

Figure 11:
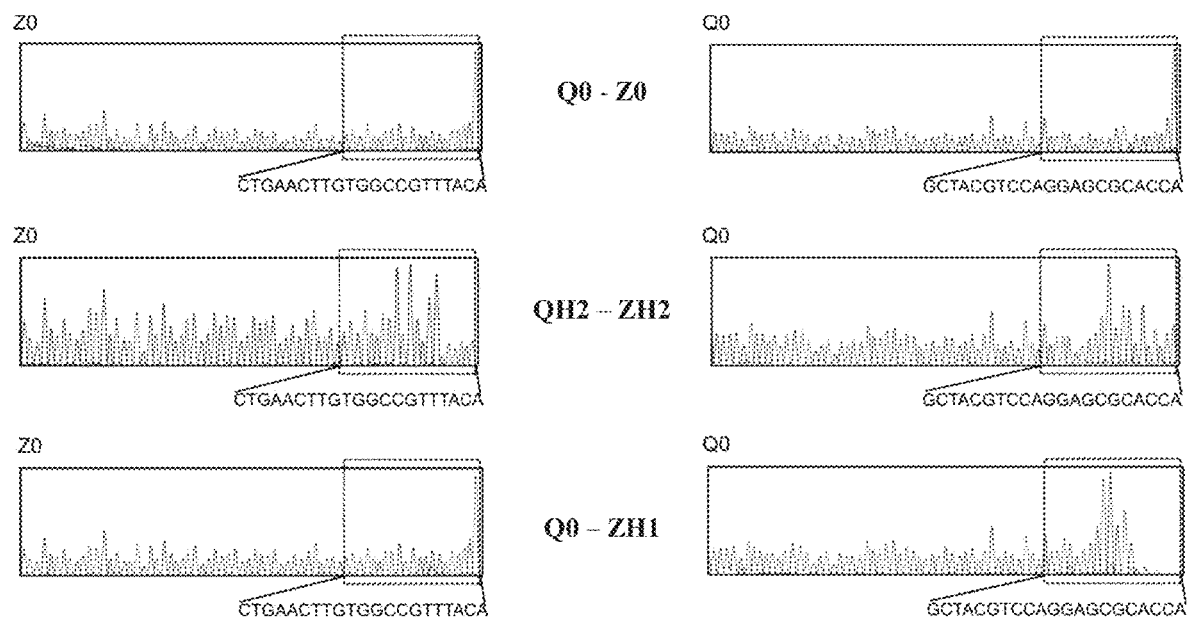
FIG. 11 illustrates that the presence of phosphoryl guanidine moieties does not cause mutations due to the interaction of the enzyme with modified monomers in the synthesis of a strand complementary to the initial primer sequence. The figure presents the result of Sanger sequencing of the DNA products after amplification in the presence of pairs of standard primers (Q0-Z0) and pairs containing phosphoryl guanidine derivatives of oligonucleotides (shown in the center figures) using native oligonucleotide primers Q0 (column on the right) and Z0 (column on the left). The frame indicates the region of the initial primers; the sequences of all primers are shown in FIG. 2.

Upon completion of amplification, the purification of PCR products and sequencing thereof by the method of Sanger according to the standard procedure using fluorescently labeled terminators BigDye 3.1 were carried out. Native oligonucleotide primers Q0 and Z0 were used for sequencing. FIG. 11 shows the results of Sanger sequencing of the DNA products after amplification in the presence of pairs of primers shown in the center using native oligonucleotide primers Q0 (column on the right) and Z0 (column on the left). The frame indicates the region of the initial primers.

It was seen (FIG. 11) that the nucleotide composition of the growing DNA strand in the presence of pairs of the native primers corresponds to the composition obtained in the presence of pairs, in which one or both primers contain PG. The presence of PG in the initial primer did not cause mutations in the growing DNA strand when extending the complementary strand in the primer region. At the same time, the presence of consecutive PGs in adjoining positions terminated the extension of the growing strand on the modified template and allowed to control the length of the final product, forming single-stranded "sticky ends", as described in Example 7.

Example 10. Use of PG Oligonucleotides as Primers for DNA Polymerases Used in Commercial PCR Systems Three commercial systems were selected to demonstrate the use of PG oligonucleotides as primers. System I contained DNA polymerase Pfu (Sileks, Russia); system II contained a mixture of polymerases Taq and Pfu for PCR of long fragments (PCR of the "Long Range" type) (Biolabmix, Russia); system III for PCR on whole blood "InBlood PCR kit" (Evrogen, Russia) with polymerase "InBlood" (Evrogen, Russia).

For systems I and II, 1 ng of plasmid DNA containing the eGFP gene was used as a template, amplification was performed in the following mode: preliminary denaturation of 95° C. for 5 min, 32 cycles: 9° C. for 10 seconds, 61° C. for 10 seconds, 72° C. for 10 seconds.

For system III, preparations of human whole blood and blood plasma containing previously added 0.2 ng of plasmid DNA per 1 µl of body fluid in the ratio of 2% (for blood plasma only) were used as a template, 5%, 10%, 20%, and 25% of the total volume of the reaction mixture in 25 µl. Amplification was carried out in the mode of 95° C. for 5 min, 26 cycles: 95° C. for 10 seconds, 61° C. for 10 seconds, 72° C. for 10 seconds.

The primer pairs used were (Q0-Z0), (Q0-ZH2), (QH2-Z0), (QH2-ZH2). Oligonucleotide sequences are shown in FIG. 2.

The results of the analysis of the PCR products by agarose gel electrophoresis are presented in FIG. 12 (where M is a marker of DNA lengths from 100 to 500 bp). It was seen (FIGS. 12 A and B) that using PG oligonucleotides as primers in the presence of various commercial polymerases and buffer mixtures, the PCR product of a given length was specifically formed. PG oligonucleotides were suitable for PCR in body fluids. The present results allow to conclude that it is possible to efficiently use PG-modified oligodeoxyribonucleotides as primers in PCR catalyzed by various DNA polymerases used in commercial PCR systems.

Example 11. PG Oligonucleotides as Primers for RNA-Dependent DNA Polymerases (Revertases)

This example demonstrated the possibility of use of PG oligonucleotides P7-P24 labeled with fluorescein as primers for the detection of hepatitis C virus (HCV) RNA as compared to the native oligonucleotide P0. Oligonucleotide sequences are shown in FIG. 2. Modified PG primers contained from 7 (from the 5' end of the oligonucleotides) to 21 consecutive PGs.

Fresh blood serum of HCV-infected donors was used as a starting material for analysis. HCV RNA was isolated using the kit "RealBest" Extraction 100 (Vector-Best, Russia) and introduced into the RT-PCR reaction according to the described procedure using either native oligonucleotide P0 or PG oligonucleotides P7-P21 and revertase (MMLV or HIV-p66) at the reverse transcription stage. The reverse transcription reaction (50 µl) was carried out in a mixture of the following composition: PG oligonucleotides (0.5 µM), MgCl$_2$ (3 mM), Tris-HCl (50 mM) pH 8.0, (NH$_4$)$_2$SO$_4$ (10 mM), KCl (30 mM), 0.01% Tween-20, set of dNTP triphosphates (0.4 mM each), BSA 100 µg/ml, MMLV or HIV-p66 (10 units of activity). The reverse transcription reaction was carried out in at least two duplicates in the following temperature mode: 45° C. for 30 min, 95° C. for 3 min.

Next, the obtained cDNA was used for PCR of the HCV-specific fragment. PCR was carried out in a mixture of the following composition: primers CTCCCGGGAGAGC-CATAG and TCCAAGAAAGGACCCGGTC (0.5 µM each), buffer (MgCl$_2$ (3 mM), Tris-SO$_4$ (50 mM) pH 8.0, (NH$_4$)$_2$SO$_4$ (10 mM), KCl (30 mM), 0.01% Tween-20), Taq DNA polymerase (1 unit of activity), fluorescently labeled hydrolysable probe 5'-ROX-TCTGCGGAACCGGT-GAGTACACCG-(BHQ2) (0.25 µM), SYBR Green I (at a dilution of 1/10000) or SYTO-13 (at a dilution of 1/2500). Amplification was carried out in the mode of 50° C. for 2 min, 49 cycles: 94° C. for 10 seconds, 60° C. for 20 seconds, 5° C. for 5 seconds, 95° C. for 1 min. The process of HCV detection using a CFX96 instrument (BioRad, USA) and the RealBest HCV RNA kit was carried out in the real-time mode via two channels: ROX is specific detection of a fluorescently labeled hydrolysable probe and FAM is non-specific detection of dsDNA using SYBR Green I dye (FIG. 13, normal style) or SYTO-13 (FIG. 13, highlighted in bold and color). As a result of amplification, a 79 bp DNA fragment was obtained that had a melting point of 86-88° C. under PCR buffer conditions.

Comparison of substrate properties of the PG oligonucleotides and the native oligonucleotide as primers was carried out by determining the reaction threshold cycle value Ct (threshold cycle), which is shown in FIG. 13. The Ct value was calculated as described previously in Example 6. It was seen that PG oligonucleotides can act as primers when obtaining cDNA on the analyzed RNA template using RNA-dependent DNA polymerases (MMLV and HIV-p66 revertases).

Example 12. PG Oligonucleotides as Primers for DNA Polymerases in One-Step RT-PCR Systems In the system for one-step RT-PCR "BioMaster RT-PCR SYBR Blue (2-)" (Biolabmix, Russia) containing MMLV revertase and thermostable DNA-dependent Taq DNA polymerase, primers specific for human U12 snRNA sequence were used.

Native oligonucleotides (U0, V0) and PG oligonucleotides (UH1, VH1, WH1) were used as primers. Oligonucleotide sequences are shown in FIG. 2. The concentration of each primer was 480-700 nM.

RT-PCR was performed on a total RNA preparation of human breast adenocarcinoma cells MCF-7 in a concentration range from 6 ng/µl to 8 pg/µl.

The reverting reaction was carried out at 45° C. for 45 minutes

Amplification mode was 95° C. for 5 min, 48 cycles: 95° C. for 10 seconds, 60° C. for 10 seconds, 72° C. for 10 seconds.

Analysis of RT-PCR products was carried out by thermal denaturation and horizontal gel electrophoresis in a 1.5% gel, followed by visualization of the nucleotide material with ethidium bromide (FIG. 14A, where is a marker of DNA lengths from 100 to 400 bp). For the analyzed primer pairs, apparent efficiency factors were determined as: 1.7 for the pair (U0-V0), 1.63 for (UH1-VH1), and 1.56 for (UH1-WH1).

It was seen (FIG. 14B) that when using PG-modified primers, the formation of non-specific amplification products with a lower melting point occurred to a much lesser extent. The results obtained demonstrated using PG oligonucleotides as primers in one-step RT-PCR systems, i.e. PG-modified primers were able to act as seeds in the RT stage (catalyzed by RNA-dependent DNA polymerase), and then in the amplification stage (catalyzed by DNA-dependent DNA polymerase).

Example 13. PG Oligonucleotides as Primers in the Amplification Reaction by the Rolling Circle Mechanism (RCA)

This example demonstrates a comparison of the efficiency of DNA amplification reaction by the rolling circle mechanism (RCA) when using PG oligonucleotides and a native oligonucleotide.

Amplification of DNA plasmid pUC19 (0.2 ng) was carried out in a reaction buffer containing Tris-HCl (50 mM) pH 7.5, MgCl$_2$ (10 mM), (NH$_4$)$_2$SO$_4$ (10 mM), DTT (4 mM), in the presence of set of deoxynucleoside triphosphates (0.2 mM each), BSA (200 ng/µl), intercalating dye SYBR Green I, DNA polymerase phi29 (0.5 units of activity/µl), 1 µm of one of the primers.

Amplification mode was 14 hours at 30° C.

PG oligonucleotides D2 and D3 and native oligonucleotide D0 were used as primers. Oligonucleotide sequences are shown in FIG. 2. Modified PG primers contained 2 and up to 3 consecutive PGs on the 3' end of the oligonucleotide.

Figure 15:
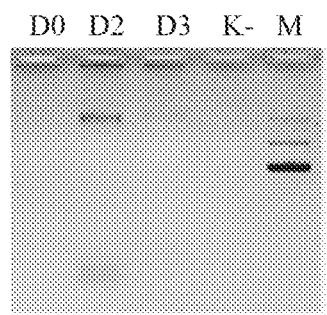
FIG. 15 illustrates the result of the use of phosphoryl guanidine derivatives of oligonucleotides as primers in rolling circle amplification reaction (RCA). The figure presents the result of electrophoretic analysis (A) and amplification factors of the rolling circle reaction products using a standard primer (D0) and phosphoryl guanidine derivatives (D2 and D3) specific for the sequence of plasmid pUC19; primer sequences are shown in FIG. 2. "K−" corresponds to the results of the control reaction without primers. M is a control for the mobility of the initial plasmid

The amplification products were analyzed by agarose gel electrophoresis in 0.8% agarose using 200 ng of plasmid pUC19 as a marker (M). The results of the analysis are presented in FIG. 15A, "K-" corresponds to the results of the control reaction without primers. It was seen (FIG. 15A) that, in the case of PG oligonucleotides, accumulation of the amplification product was observed. At the same time, the amplification product (for each primer D2, D3, and D0) was diluted $3 \times 10^{-6}$ times and 50 µl of the obtained solution was used to estimate the amplification factor by PCR method in nine duplicates in the real-time mode in the presence of a fluorescently labeled hydrolysable probe to a pUC9 site $10^5$ nucleotides in length. Then, the average value of the threshold reaction cycle (Ct) and the difference (ΔCt) between the Ct of a specific primer and the dilution of the initial template corresponding to the initial conditions of the amplification reaction (amplification of DNA plasmid pUC19 in the amount of 0.2 ng) were calculated.

The obtained ΔCt value was used to calculate the RCA amplification factor with the assumption that the efficiency of the initial conditions is 1 (FIG. 11B). When comparing the data presented in the Table, it was seen that the amplification factor was higher when using PG oligonucleotides D2 and D3 than of original native primer D0, namely, 247.3 and 29.9, respectively, compared to 9.4.

Example 14. Increasing the Selectivity of Mutation Detection Using PG Oligonucleotide as a Primer in Allele-Specific PCR Amplification of the template was carried out in a buffer containing Tris-HCl (65 mM) pH 8.9; (NH$_4$)$_2$SO$_4$ (24 mM); MgSO$_4$ (3 mM), 0.05% Tween-20, set of deoxynucleoside triphosphates (0.2 mM each), Taq DNA polymerase (0.03 units of activity/µl), fluorescently labeled hydrolysable probe 5'-HEX-CTGTATCGTCAAGGCACTCTTGC-BHQ2-3' (100 nM).

Amplification mode was 95° C. for 3 min, 50 cycles: 95° C. for 10 seconds, 60° C. for 40 seconds.

2 ng of human genomic DNA isolated from a histological block with colorectal cancer tissue, with or without the addition of a control plasmid containing mutation c.38G>A (G13D) in the KRAS gene fragment (GACTGAATATAAACTTGTGGTAGTTGGAGCTGGTG(G/A)CGTAGGCAAGA GTGCCTTGACGATACAGCTAATTCAGAATCATTTTGTGGACGAATATG) were used as templates, in an amount of 1.1% relative to the total amount of the KRAS gene fragment in genomic DNA.

Figure 16:
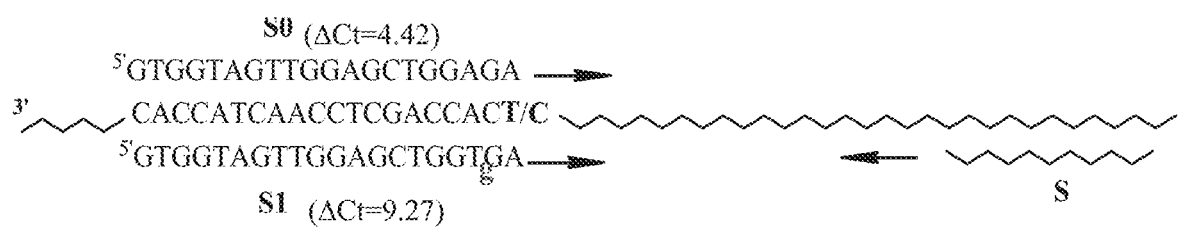
FIG. 16 shows an increase in selectivity of identification of a mutation using phosphoryl guanidine derivatives of oligonucleotides as a primer in allele-specific PCR. The figure presents a schematic representation of an experiment to identify the single nucleotide mutation T/C in the KRAS gene in genomic DNA by allele-specific PCR in the presence of a pair of standard primers S0+S and a pair of standard and phosphoryl guanidine derivative S1+S. The primer sequences are shown in FIG. 2. The ΔCt value is indicated next to the primer designation.

Pairs of oligonucleotides (forward+reverse) were used as primers: native oligonucleotides S0+S and S1+S, where S and S0 are native oligonucleotides, S1 is a PG oligonucleotide. Each primer was added to the reaction mixture at a concentration of 300 nM. Primer structure is shown in FIG. 2. A schematic representation of the detection of the single nucleotide mutation T/C in the template using method of allele-specific PCR in the presence of pairs of primers S0+S and S1+S is shown in FIG. 16.

The selectivity of mutation detection was determined by real-time PCR using a LightCycler 96 instrument (Roche, Switzerland).

For each pair of primers, the average value of the threshold reaction cycle (Ct) and the difference (ΔCt) between the sample containing 1.1% mutation and the sample without mutation were calculated. It was found that the ΔCt of the pair (S1+S) was 9.27, while (S0+S) was 4.42 (FIG. 16, the ΔCt value is indicated next to the designation of the corresponding primers). Thus, it can be concluded that the selectivity of the pair containing the PG oligonucleotide was higher than that of the pairs based on the native oligonucleotides.

LIST OF REFERENCES CITED

1. Saiki R. K., Scharf S., Faloona F., Mullis K. B., Horn G. T., Erlich H. A., Arnheim N. Enzymatic amplification of beta-globin genomic sequences and restriction site analysis for diagnosis of sickle cell anemia//Science.—1985.—V. 230.—P. 1350-1354.
2. Mullis K. B., Faloona F. A. Specific synthesis of DNA in vitro via a polymerase-catalyzed chain reaction.//Methods Enzymol.—1987.—V. 155.—P. 335-350.
3. Ballantyne K. N., van Oorschot R. A., Mitchell R. J. Locked nucleic acids in PCR primers increase sensitivity and performance//Genomics.—2008.—V. 91.—P. 301-305.
4. Brent C. Satterfield cooperative primers: 2.5 million-fold improvement in the reduction of non-specific amplification//J. Mol. Diagn.—2014.—V. 16.—P. 163-173.
5. Bodepudi V., Schoenbrunner N. J., Will S. Methods and reagents for reducing non-specific amplification//WO 2013091835 A1, 27 Jun. 2013.
6. Schneider U. V., Mikkelsen N. D., Lindqvist A., Okkels L. M., Johnk N., Lisby G. Improved efficiency and robustness in qPCR and multiplex end-point PCR by twisted intercalating nucleic acid modified primers//PLoS One.—2012.—V. 7.—e38451.
7. Wanli Bi. Nucleic acid amplification using a reversibly modified oligonucleotide//U.S. Pat. No. 8,334,099 B2. 18 Dec. 2012.
8. Lebedev A. V., Paul N., Yee J., Timoshchuk V. A., Shum J., Miyagi K., Kellum J., Hogrefe R. I., Zon G. Hot start PCR with heat-activatable primers: a novel approach for improved PCR performance//Nucleic Acids Res.—2008.—V. 36.—e131.
9. Summerton J., Stein D., Huang S. B., Matthews P., Weller D., Partridge M. Morpholino and phosphorothioate antisense oligomers compared in cell-free and in-cell systems//Antisense Nucleic Acid Drug Dev.—1997.—V. 7.—P. 63-70.
10. Chan H. W.-H., Yang Y.-S., Chen W.-Y. Partially neutral single-stranded oligonucleotide//US 20170015699 A1, January 2017.
11. Robinson P. S., Holme J., Jain N. Polymerase chain reaction detection system using oligonucleotides comprising a phosphorothioate group//WO2013140107 A1, 26 Sep. 2013.
12. Stetsenko D., Kupryushkin M., Pyshnyi D. Modified oligonucleotides and methods for their synthesis//WO 2016028187 A1, publication date 25 Feb. 2016.

13. Kupryushkin M S, Pyshnyi D V, Stetsenko D. A. Phosphoryl guanidines. A new class of nucleic acid analogues//Acta Naturae.—2014.—V. 6.—No. 4.—P. 116-118.
14. Kuznetsov N. A., Kupryushkin M. S., Abramova T. V., Kuznetsova A. A., Miroshnikova A. D., Stetsenko D. A., Pyshnyi D. V, Fedorova O. S. New Oligonucleotide Derivatives as Unreactive Substrate Analogues and Potential Inhibitors of Human Apurinic/Apyrimidinic Endonuclease APE1//Molecular BioSystems.—2016.—V. 12.—N1.—P. 67-75.

We claim:

1. A method for template-based enzymatic DNA synthesis, wherein a primer containing at least one phosphoryl guanidine group corresponding to the General formula (I):

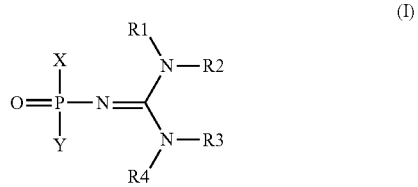

where,
each X and Y is independently selected from nucleoside or oligonucleotide; and
each of the substituents R1, R2, R3, and R4 can be hydrogen atom H or $C_1$-$C_5$ alkyl, or any two from R1-R4, together to form $C_2$-$C_5$ alkanediyl, is used to initiate the reaction.

2. The method for template-based enzymatic DNA synthesis according to claim 1, which method is used for amplification of nucleic acids.

3. The method for template-based enzymatic DNA synthesis according to claim 1, which method is used for carrying out polymerase chain reaction.

4. The method for template-based enzymatic DNA synthesis according to claim 1, which method is used for carrying out allele-specific polymerase chain reaction.

5. The method for template-based enzymatic DNA synthesis according to claim 1, which method is used for reverse transcription.

6. The method for template-based enzymatic DNA synthesis according to claim 1, which method is used in both stages of reverse transcription and subsequent polymerase chain reaction.

7. The method for template-based enzymatic DNA synthesis according to claim 1, which method is used for amplification of nucleic acids by the rolling circle mechanism.

8. A reaction mixture for template-based enzymatic DNA synthesis according to claim 1 further comprising a primer containing at least one internucleotide phosphoryl guanidine group corresponding to the formula (I).

9. A set of reaction mixtures for template-based enzymatic DNA synthesis according to claim 1 further comprising a primer containing at least one internucleotide phosphoryl guanidine group corresponding to the formula (I).